(12) United States Patent
Chaing

(10) Patent No.: US 9,675,442 B2
(45) Date of Patent: Jun. 13, 2017

(54) OPTIMIZED INJECTOR OF BREAST IMPLANT INJECTOR

(71) Applicant: Yu-Ming Chaing, Kaohsiung (TW)

(72) Inventor: Yu-Ming Chaing, Kaohsiung (TW)

(*) Notice: Subject to any disclaimer, the term of this patent is extended or adjusted under 35 U.S.C. 154(b) by 211 days.

(21) Appl. No.: 14/793,746

(22) Filed: Jul. 8, 2015

(65) Prior Publication Data

US 2016/0008125 A1 Jan. 14, 2016

(30) Foreign Application Priority Data

Jul. 11, 2014 (TW) .............................. 103212346 A

(51) Int. Cl.
- *A61F 2/12* (2006.01)
- *A61M 37/00* (2006.01)
- *A61D 7/00* (2006.01)
- *A61M 5/315* (2006.01)
- *A61M 5/32* (2006.01)

(52) U.S. Cl.
CPC ............. *A61F 2/12* (2013.01); *A61M 5/3158* (2013.01); *A61M 5/32* (2013.01)

(58) Field of Classification Search
CPC .............. A61F 2/12; A61F 7/00; A61M 37/00
USPC ...................................... 623/7–8; 604/57–59
See application file for complete search history.

(56) References Cited

U.S. PATENT DOCUMENTS

| | | | | |
|---|---|---|---|---|
| 6,530,896 B1* | 3/2003 | Elliott | ...................... | A61D 7/00 604/60 |
| 8,585,733 B2* | 11/2013 | Newell | .............. | A61B 17/0401 606/192 |
| 2012/0179250 A1* | 7/2012 | Brennan | .................... | A61F 2/12 623/8 |
| 2013/0220801 A1* | 8/2013 | Joshi | .................. | A61B 17/3478 204/242 |
| 2013/0267931 A1* | 10/2013 | Nazzaro | ............ | A61M 37/0069 604/506 |
| 2013/0317610 A1* | 11/2013 | Ledergerber | .............. | A61F 2/12 623/8 |
| 2014/0094767 A1* | 4/2014 | Wallace | ............ | A61M 37/0069 604/506 |
| 2015/0039086 A1* | 2/2015 | Ledergerber | .......... | B29C 59/021 623/8 |
| 2015/0297339 A1* | 10/2015 | Placik | ........................ | A61F 2/12 623/8 |
| 2016/0206445 A1* | 7/2016 | Gheevarughese | .... | A61F 2/3094 |
| 2016/0250019 A1* | 9/2016 | Anderson | .................. | A61F 2/12 623/8 |
| 2016/0354125 A1* | 12/2016 | McLean | ............. | A61B 17/7032 |
| 2016/0374798 A1* | 12/2016 | Nguyen | ..................... | A61F 2/12 623/8 |

* cited by examiner

*Primary Examiner* — Suzette J Gherbi

(57) ABSTRACT

An optimized breast implant injector includes a hollow tube body and a plunger. The hollow tube body has a short tube reducer at one end and a circular disk at the other end. The plunger includes a push block, a driving device, and two fixed covers. The outer surface of the push block appears to be a circular arc shape. The driving device includes a rotating part, and a driving gear, a driven gear and a rack that mesh together. A user uses the rotating part to easily start the driving gear, the driven gear, and the rack, in order to let the rack drive the push block to move the breast implant in the hollow tube body. Through operating a short tube reducer of the hollow tube body and the push block, the breast implant can be pushed through from the short tube reducer easily.

9 Claims, 9 Drawing Sheets

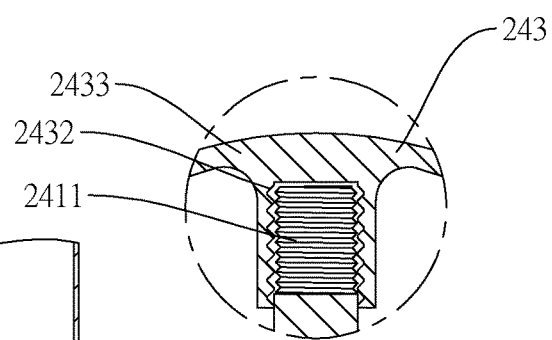
FIG.4A
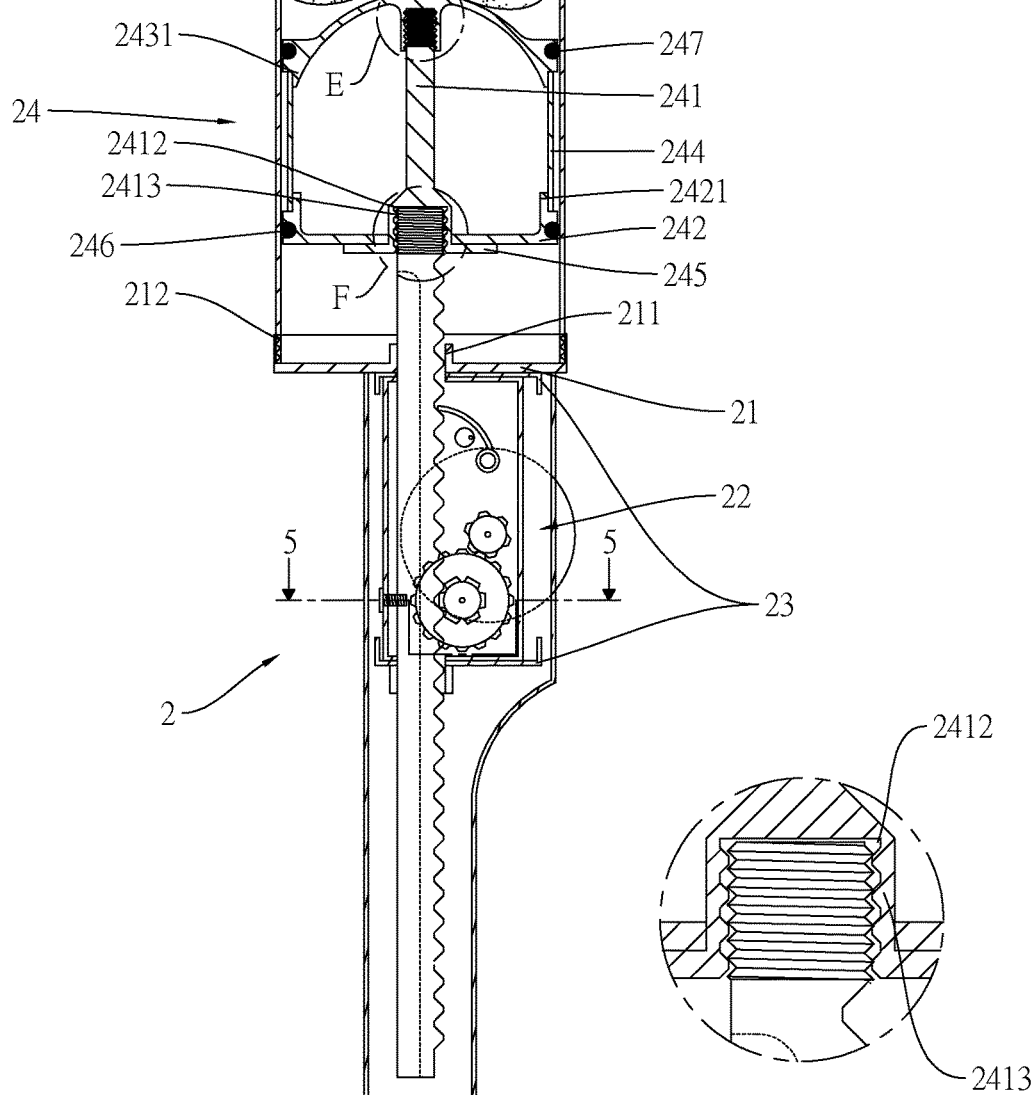
FIG.4
FIG.4B

OPTIMIZED INJECTOR OF BREAST IMPLANT INJECTOR

BACKGROUND OF THE INVENTION

1. Field of the Invention

The invention relates to breast implant injectors and more particularly to a an optimized breast implant injector, which provides an injector to deliver the silicone breast implant to the patient's submammary pocket with ease, thus to reduce the operation time and risk, and to offer the medical staff an optimized breast implant injector to use conveniently.

2. Description of Related Art

There is a conventional silicon breast implant injector for augmentation mammaplasty commercially available. It describes a hollow tube and a plunger wherein the hollow tube has a barrel which has one end tapered to form a first arched barrel connecting to an inverse second arched barrel which in turn is connected to an ejection opening formed at the same diameter as the second arched barrel but into a short inflexible length tube. The plunger can push a silicon breast implant, coated with a lubricating fluid non-irritating to human body, held in the hollow tube through an incision into patient's submammary pocket. Coupled with a smooth connection between the first arched barrel and the second arched barrel, push resistance can be reduced during the insertion process. However, although the breast implant is in a liquid state, its hardness and density is different from those fluid materials of low density and low hardness. Even coated with a lubricating fluid non-irritating to human body, generally the medical staffs still will not easily push the plunger without applying much strength. As a result, the risk of lengthening the operation increases and, in case of accidentally charged force happens, it may harm the body.

SUMMARY OF THE INVENTION

The main objective of the invention is to provide a labor-saving injector mainly through the coordination of a set of gears, so that the level of force applied by the user to push the breast implant forward can be reduced and, as a result, the risk of operation is reduced and the augmentation mammaplasty surgery can be more smoothly and easily.

Another objective of the invention is to provide an injector that can increase the level of smoothness, when the breast implant is pushed forward, as well as the safety and success rate of the operation.

In accordance with the aforementioned objectives, the optimized breast implant injector of the invention mainly comprises a hollow tube body and a plunger wherein the hollow tube body has a short tube reducer at one end and an outer thread located at the outer diameter at the other end. The outer thread is crewed into the inner thread of a circular disk wherein the circular disk is equipped with a protruding channel. The plunger comprises a push block, a driving device and two fixed covers.

The push block located inside the hollow tube body comprises a rod, a bottom push block, a sleeve and a top push block. The top of the rod has an outer thread and the bottom of the rod has a first concave part wherein the first concave part has an inner thread and the peripheral edge of the first concave part has a bearing disk. The bottom push block encases the rod and is supported by the bearing disk, wherein the side edge of the bottom push block has a top clamping part and a padding ring that forms a close contact with the inner surface of the hollow tube body. The bottom edge of the sleeve is sleeved on the top clamping part of the bottom push block. The inner side of the top push block has a second concave part and the inner surface of the second concave part has an inner thread that is screwed into the outer thread of the top of the rod. In addition, the side edge of the top push block has a bottom clamping part, which is sleeved by the top edge of the sleeve, and a padding ring that forms a close contact with the inner surface of the hollow tube body.

The driving device comprises a housing, a rotating part, a driving gear, a driven gear, a rack, a retaining piece and a eccentric shaft. The housing has a top opening and a bottom opening corresponding to the channel. The rotating part is located in the outer side of the housing. The driving gear, the driven gear, and the rack are located inside the housing. The retaining piece is coupled to the inner surface of the housing and the free end of the retaining piece is connected with the rack. The eccentric shaft penetrates and is mounted on the housing, and exists in the inside and outside of the housing. The rotating part is coaxially coupled to the driving gear; the driving gear is in mesh with the driven gear; the driven gear is meshing to the rack; and one end of the rack has an outer thread.

Each fixed cover is connected to the top opening and the bottom opening of the housing separately; each fixed cover is provided with an opening corresponding to the top opening and the bottom opening separately, wherein both ends of the rack enter through the top opening and the bottom opening of the housing separately and the openings of the fixed covers separately, so that one end of the rack can enter into the channel of the circular disk and the outer thread of the rack can screwed into the inner thread of the first concave part.

The aforementioned housing, the circular disk, and each fixed cover can be connected by glue or using a locking element to lock together. The hollow tube body and the short tube reducer can be made as one piece to increase the strength and to reduce the connection gap. Furthermore, the aforementioned driven gear includes a large gear and a small gear, both mounted coaxially to the same shaft, having the large gear meshing to the driving gear; the small gear meshing to the rack; and the diameter of the driving gear being smaller than that of the large gear. Therefore, according to the principle of moments, the operation between the large gear and the small gear allows the user to easily rotate the rotating part, causing the rotating part to roll the driving gear and the driven gear, thus to indirectly drive the rack forward to move the push block in the hollow tube body, so that the push block pushes the breast implant forward and consequently the efficiency is improved due to less force being needed for pushing the breast implant.

The bottom of the aforementioned rack can have a groove and a locking element is locked from the outer side of the housing to the inside of the groove, so that the locking element and the groove are mutually restrained. Consequently, the rack can steadily move forward and backward as to increase the stability of transporting the breast implant. The outer of the driving device can be installed with a protective case for enhancing the beauty and protection function.

Through the coordination of the short tube reducer of the hollow tube body along with the top push block whose outer surface is in a circular arc shape, the gap between the short tube reducer and the push block can be effectively reduced, so that the breast implant can easily be pushed through and implanted in the patient's body and the safety and success rate of surgery can be increased The above and other objects, features and advantages of the invention will become apparent from the following detailed description taken with the accompanying drawings.

BRIEF DESCRIPTION OF THE DRAWINGS

FIG. 4 is a schematic view of the embodiment of the invention;

FIG. 4A is a detailed view of the area in circle E of FIG. 4;

FIG. 4B is a detailed view of the area in circle F of FIG. 4;

DETAILED DESCRIPTION OF THE INVENTION

Figure 1:
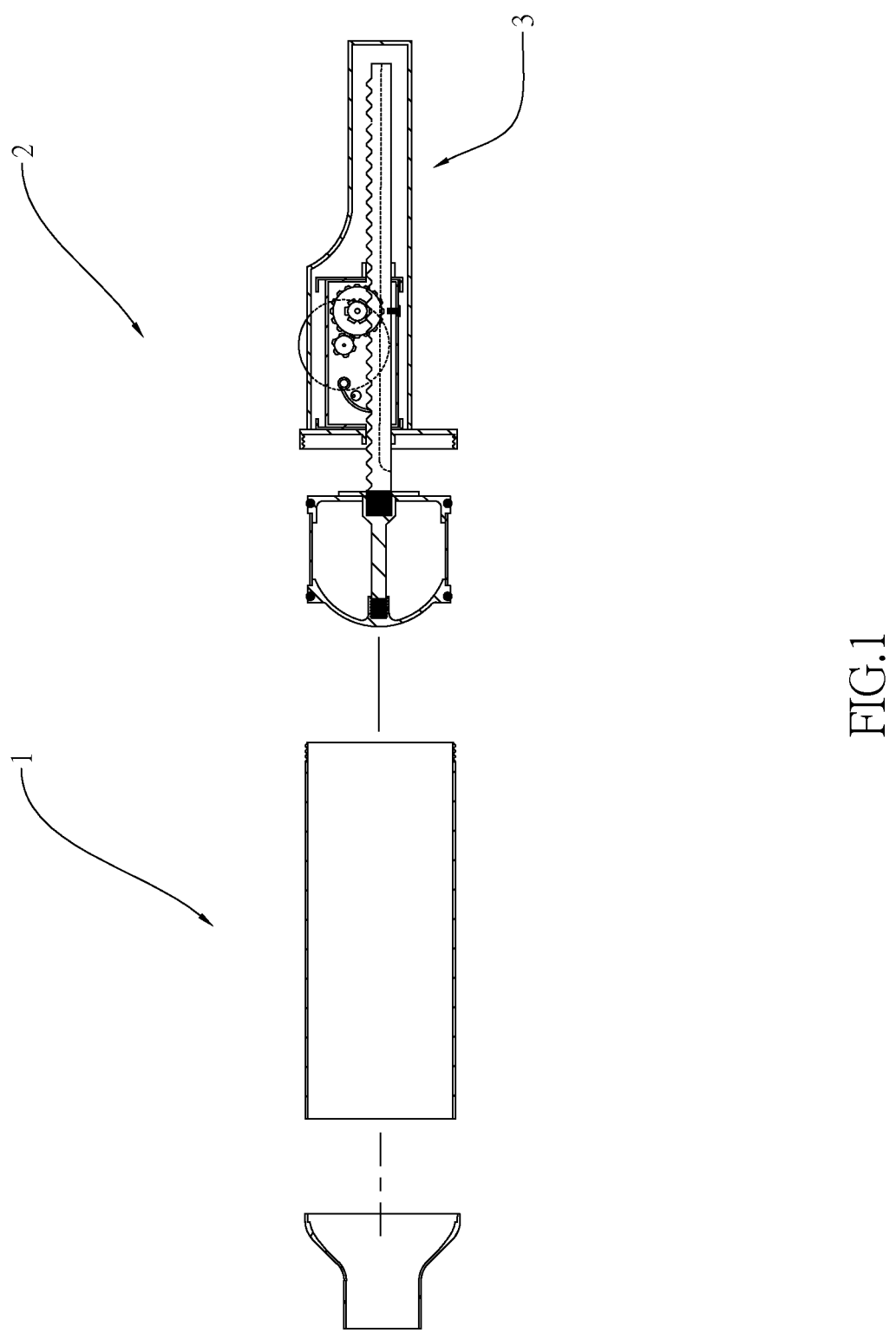
FIG. 1 is an exploded of the invention.
Figure 2:
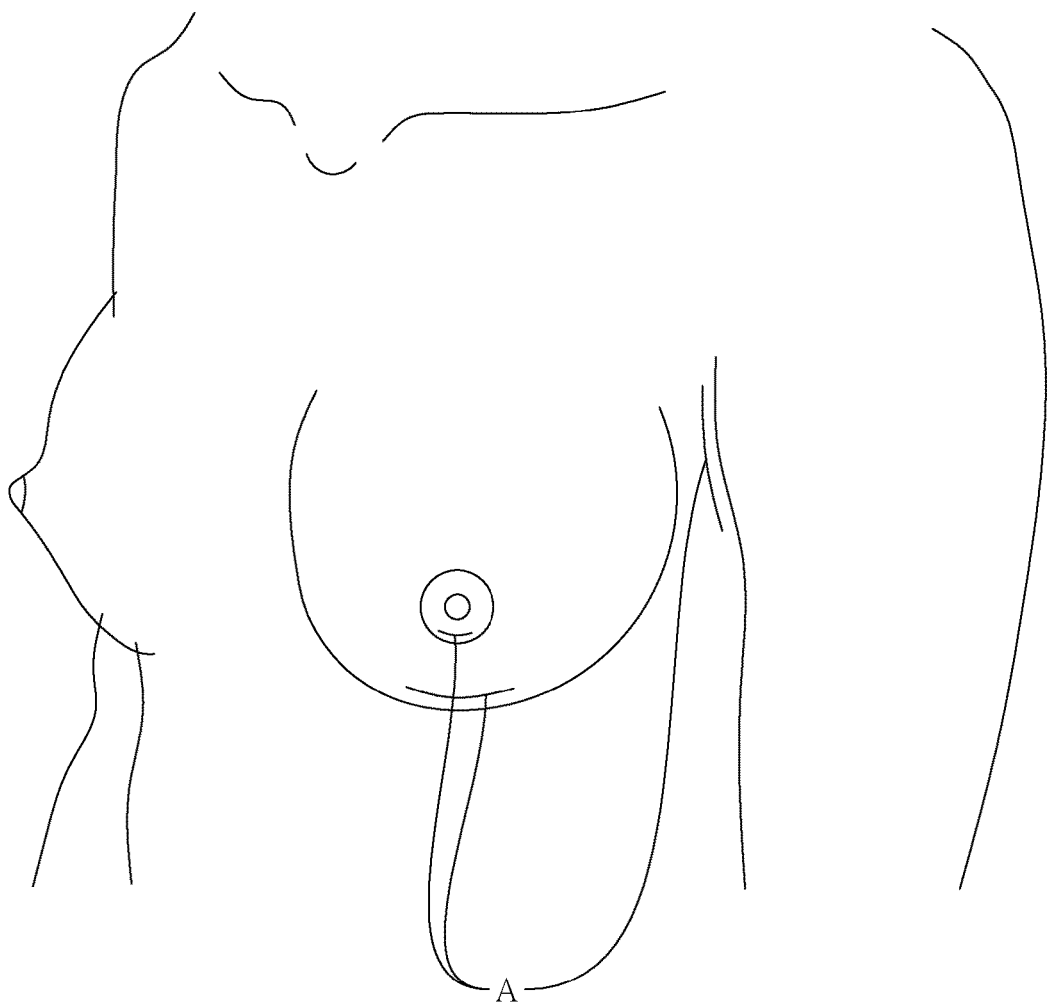
FIG. 2 is a schematic view of the incisions of a patient's body.
Figure 3A:
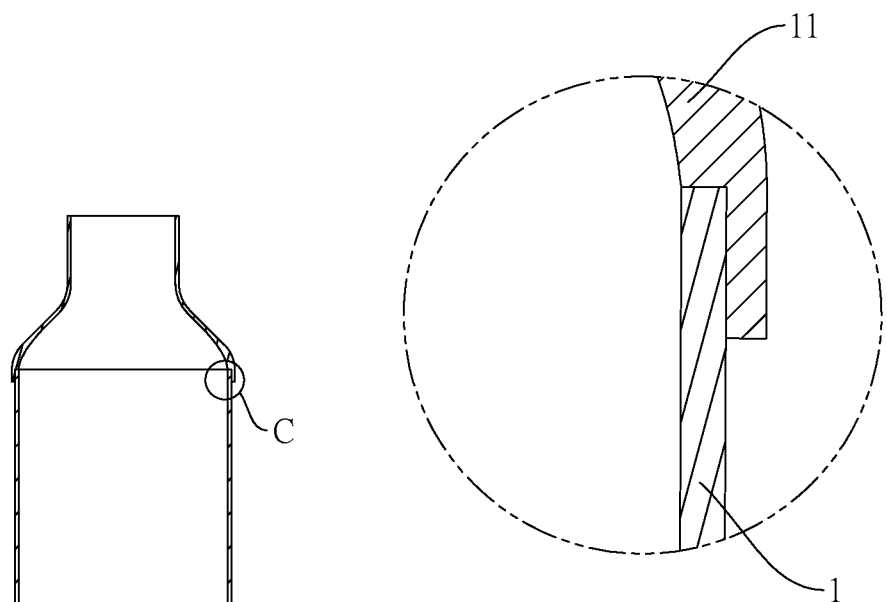
FIG. 3A is a detailed view of the area in circle C of FIG. 3.
Figures 3, 3B:
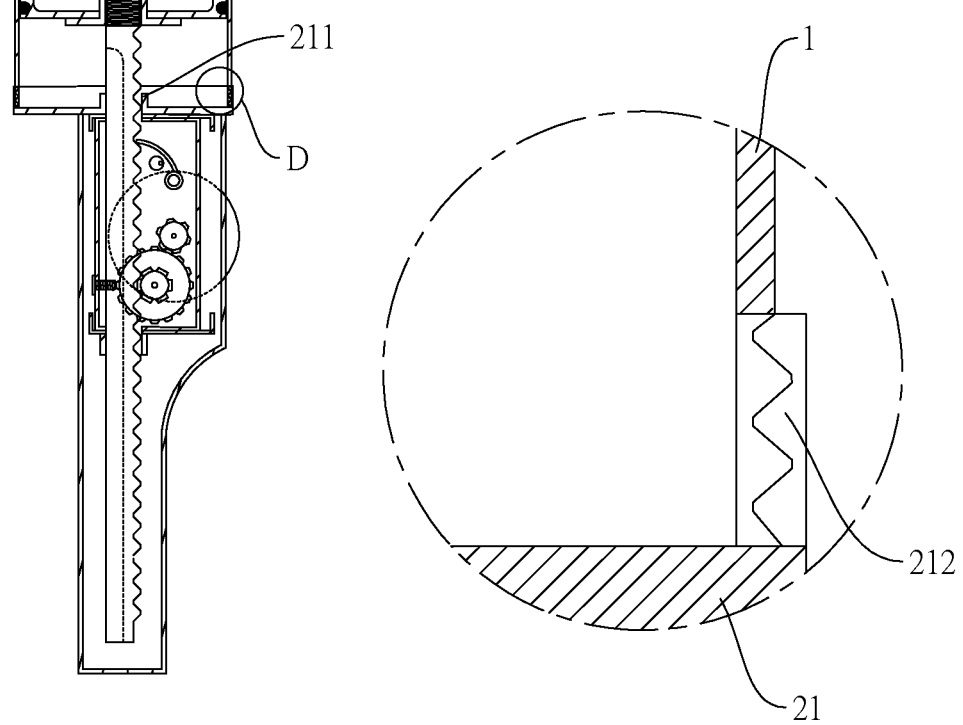
FIG. 3 is a combined schematic view of the short tube reducer and the hollow tube body, the hollow tube body and the plunger of the invention.
FIG. 3B is a detailed view of the area in circle D of FIG. 3.

Referring to FIGS. 1 and 2, an optimized breast implant injector of the invention mainly comprises a hollow tube body 1 and a plunger 2. The outer of the plunger 2 can be installed with a protective case 3 for enhancing the beauty and protection function according to the needs. The aforementioned optimized breast implant injector can push the breast implant quickly through the device and the incision A into the submammary pocket during the surgery (the incision A in FIG. 2 is for demonstration only and the actual location shall be decided by the medical professions), in order to increase the operational convenience for the surgeons, and safety and the success rate of the operation Referring to FIGS. 3, 3A and 3B, the hollow tube body 1 has a short tube reducer 11, which can be sleeved on the hollow tube body 1, at one end. Through the design of the short tube reducer 11, the breast implant can be facilitated to quickly be squeezed from the ejection opening. The other end of the hollow tube body 1 has an outer thread 12 located at the outer diameter. The outer thread 12 is crewed into the inner thread 212 of a circular disk 21. The circular disk 21 is equipped with a protruding channel 211 whereas the hollow tube body 1 and the short tube reducer 11 not only are coupled to each other, but also can be made as one piece according to the needs, to increase the strength and to reduce the connection gap.

Referring to FIGS. 4 to 7, the aforementioned plunger 2 comprises a push block 24, a driving device 22 and two fixed covers 23. The push block 24 comprises a rod 241, a bottom push block 242, a sleeve 244 and a top push block 243. The top of the rod 241 has an outer thread 2411 and the bottom of the rod 241 has a first concave part 2412 wherein the first concave part 2412 has an inner thread 2413 and the peripheral edge of the first concave part 2412 has a bearing disk 245. The bottom push block 242 encases the rod 241 and is supported by the bearing disk 245, wherein the side edge of the bottom push block 242 has a top clamping part 2421 and a padding ring 246 that forms a close contact with the inner surface of the hollow tube body 1. The bottom edge of the sleeve 244 is sleeved on the top clamping part 2421 of the bottom push block 242. The inner side of the top push block 243 has a second concave part 2432 and the inner surface of the second concave part 2432 has an inner thread 2433 that is screwed into the outer thread 2411 of the top of the rod 241. In addition, the side edge of the top push block 243 has a bottom clamping part 2431, which is sleeved by the top edge of the sleeve 244, and a padding ring 247 that forms a close contact with the inner surface of the hollow tube body 1.

Figure 5:
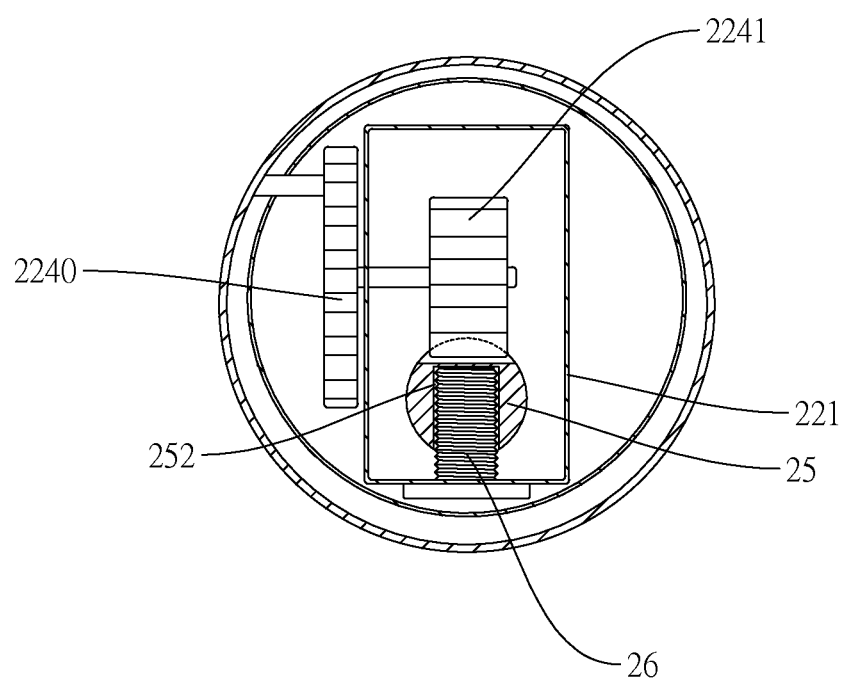
FIG. 5 is a cross-sectional view taken along line 5-5 of FIG. 4.

The driving device 22 comprises a housing 221, a rotating part 222, a driving gear 223, a driven gear 224, a rack 25, a retaining piece 225, and an eccentric shaft 226, wherein the housing 221 has a top opening 2211 and a bottom opening 2212 corresponding to the channel 211. The rotating part 222 is located in the outer side of the housing 221. The driving gear 223, the driven gear 224, and the rack 25 are located inside the housing 221. The retaining piece 225 is coupled to the inner surface of the housing 221 and the free end of the retaining piece 225 is connected with the rack 25. The eccentric shaft 226 penetrates and is mounted on the housing 221, and exists in the inside and outside of the housing 221. The rotating part 222 is coupled to the driving gear 223; the driving gear 223 is in mesh with the driven gear 224. The driven gear 224 includes a large gear 2240 and a small gear 2241 both mounted coaxially to the same shaft, having the large gear 2240 meshing to the driving gear 223; the small gear 2241 meshing to the rack 25; and the diameter of the driving gear 223 being smaller than that of the large gear 2240. One end of the rack 25 has an outer thread 251; the bottom of the rack 25 can have a groove 252. A locking element 26 is locked from the outer side of the housing 221 to the inside of the groove 252 (as shown in FIG. 5), so that the locking element 26 and the groove 252 are mutually restrained.

Each fixed cover 23 is connected to the top opening 2211 and the bottom opening 2212 of the housing 221 separately; each fixed cover 23 is provided with an opening 231 corresponding to the top opening 2211 and the bottom opening 2212 separately, whereas both ends of the rack 25 enter through the top opening 2211 and the bottom opening 2212 of the housing 221 separately and the openings 231 of the fixed covers 23 separately, so that one end of the rack 25 can enter into the channel 211 of the circular disk 21 and the outer thread 251 of the rack 25 can be screwed into the inner thread 2413 of the first concave part 2412.

Figures 6, 6A, 6B:
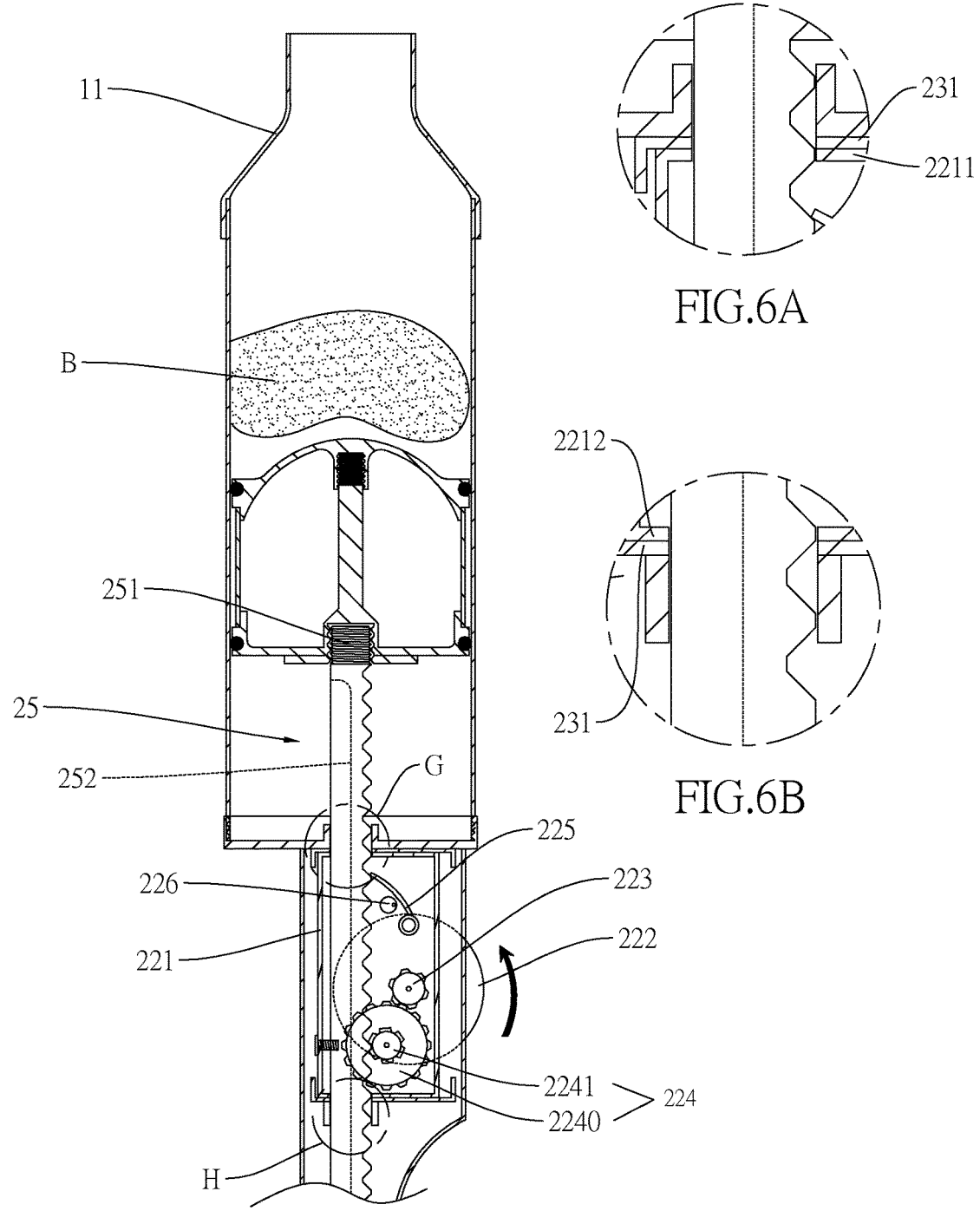
FIG. 6 is a schematic view of the embodiment of the invention.
FIG. 6A is a detailed view of the area in circle G of FIG. 6.
FIG. 6B is a detailed view of the area in circle H of FIG. 6.
Figure 7:
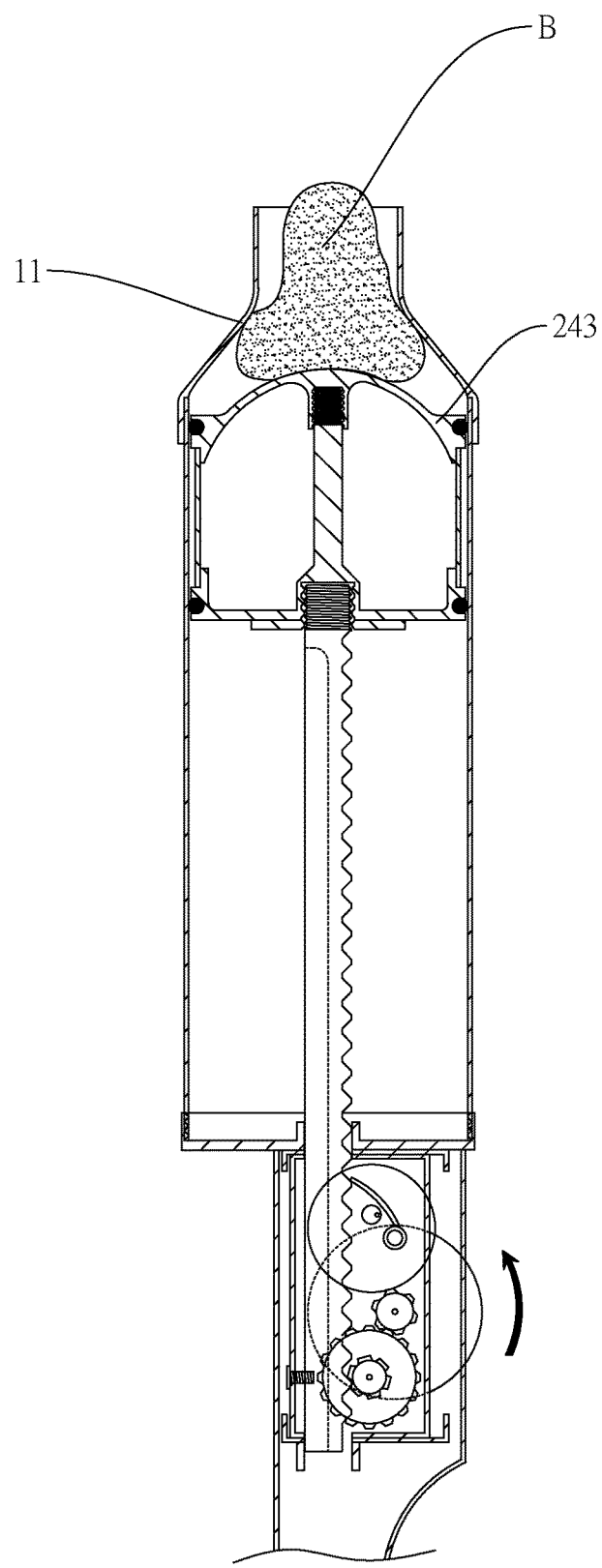
FIG. 7 is another schematic view of the embodiment of the invention.

During the implementation, according to the principle of moments on the coordination between the large gear 2240 and the small gear 2241, the user can easily rotate the rotating part 222, leading to the driving gear 223, which is mounted coaxially to the same shaft as the rotating part 222, to roll the large gear 2240 and the small gear 2241 of the driven gear 224, and eventually leading to the small gear 2241 to move the rack 25. Through the meshing of the outer thread 251 of the rack 25 and the inner thread 2413 of the push block 24, when the rack 25 moves forward or backward, the rack can conveniently and steadily move the push block 24 (under the restriction of the locking element 26 and the groove 252), so that the breast implant B located in front of the push block 24 is pushed forward (as shown in FIG. 6). When the push block 24 pushes the breast implant into the short tube reducer 11, with the guiding function of the short tube reducer 11 on the breast implant B, the process of pushing the breast implant B is more smoothly. In addition, the design of the short tube reducer 11 and the top push block 243, which has a circular arc shaped outer surface, together reduces the gap between them. When a smaller size of breast implant B is used, the operation still can be done conveniently (as shown in FIG. 7). Therefore, by coordinating the short tube reducer 11 and the push block 24 together, the breast implant B can be pushed out from the short tube reducer 11 easily and implanted to the patient's body, thus to increase the safety and success rate of the operation.

Figure 8:
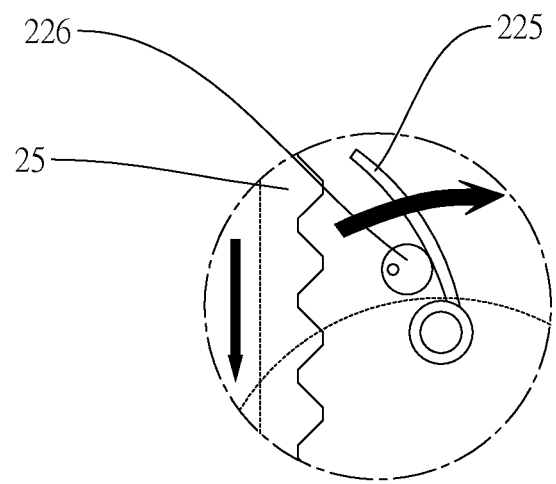
FIG. 8 is a schematic view of the retaining piece of the invention deviating from the rack.

Referring to FIG. 8 together with FIGS. 4, 4A and 4B, if the user wants to pull the push block 24 backward, the user only needs to adjust the eccentric shaft 226 to make the retaining piece 225 shifting away from the rack 25 so that the rack 25 is not restrained by the retaining piece 225 and can pull the push block 24 backward.

Figure 9:
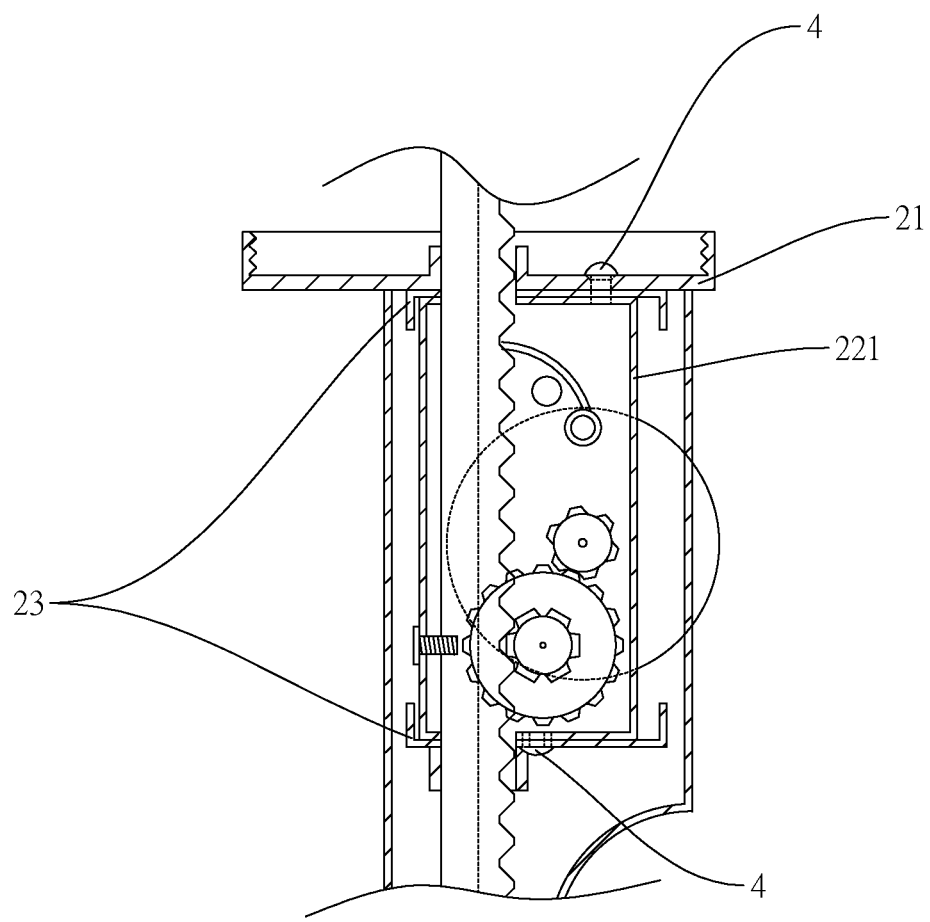
FIG. 9 is a schematic view of the housing, the circular disk, and the fixed covers of the invention locked together.

Referring to FIG. 9 together with FIGS. 4, 4A and 4B, the housing 221, the circular disk 21, and each fixed cover 23 can be connected either by glue or using a locking element 4 to lock together as needed, so that the housing 221, the circular disk 21 and each fixed cover 23 can be easily disassembled or replaced.

In summary of the aforementioned descriptions, the optimized breast implant injector has the following advantages:

The optimized breast implant injector of the invention utilizes the principle of moments in the operation of the large gear and the small gear and allows the user to move and to push the rack forward by applying force slightly, so that the push block can push the breast implant forward and, as a result, the efficiency is improved due to less force being needed for pushing the breast implant.

The optimized breast implant injector of the invention has a pushing block whose outer surface is in a circular arc shape, resulting in a better coordination of the short tube reducer of the hollow tube body and the push block, and the reduction of the gap between the short tube reducer and the push block effectively. The sizes of the breast implant pushed by the injector become plentiful. Any size of breast implant can be easily pushed through the short tube reducer and implanted in the patient's body and, as a result, the usability of the injector increases significantly.

The optimized breast implant injector of the invention has a rack, having a locking element and the groove mutually restrained at the bottom of the rack, so that the rack can steadily move forward or backward, as to increase the stability of transporting the breast implant.

While the invention has been described in terms of preferred embodiments, those skilled in the art will recognize that the invention can be practiced with modifications within the spirit and scope of the appended claims.

What is claimed is:

1. An optimized breast implant injector, comprising a hollow tube body and a plunger, wherein:
   the hollow tube body includes a short tube reducer at one end and an outer thread at the outer diameter at the other end, having the outer thread screwed to the inner thread of a circular disk and the circular disk containing a channel;
   the plunger includes a push block, a driving device, and two fixed covers; having the push block, located inside the hollow tube body, comprising a rod, a bottom push block, a sleeve and a top push block, wherein the top of the rod has an outer thread and the bottom of the rod has a first concave part; the first concave part has an inner thread and the peripheral edge of the first concave part has a bearing disk, wherein the bottom push block encases the rod and is supported by the bearing disk; the side edge of the bottom push block has a top clamping part and a padding ring that forms a close contact with the inner surface of the hollow tube body; wherein the bottom edge of the sleeve is sleeved on the top clamping part of the bottom push block; wherein the inner side of the top push block has a second concave part and the inner surface of the second concave part has an inner thread that is screwed into the outer thread of the top of the rod; the side edge of the top push block has a bottom clamping part, which is sleeved by the top edge of the sleeve, and a padding ring that forms a close contact with the inner surface of the hollow tube body;
   the driving device includes a housing, a rotating part, a driving gear, a driven gear, a rack, a retaining piece and a eccentric shaft, wherein the housing has a top opening and a bottom opening corresponding to the channel; the rotating part is located in the outer side of the housing; the driving gear, the driven gear, and the rack are located inside the housing; the retaining piece is coupled to the inner surface of the housing and the free end of the retaining piece is connected with the rack; the eccentric shaft penetrates and is mounted on the housing, and exists in the inside and outside of the housing, whereas the rotating part is coupled to the driving gear; the driving gear is in mesh with the driven gear; the driven gear is meshing to the rack; and one end of the rack has an outer thread; and
   each fixed cover is connected to the top opening and the bottom opening of the housing separately; each fixed cover provided with an opening corresponding to the top opening and the bottom opening separately, whereas both ends of the rack enter through the top opening and the bottom opening of the housing separately and the openings of the fixed covers separately, so that one end of the rack can enter into the channel of the circular disk and the outer thread of the rack can screwed into the inner thread of the first concave part.

2. The optimized breast implant injector as claimed in claim 1, wherein the housing, the circular disk, and each fixed cover can be connected by glue.

3. The optimized breast implant injector as claimed in claim 1, wherein the circular disk, each fixed cover, and the housing can be locked together using a locking element.

4. The optimized breast implant injector as claimed in claim 1, wherein the driven gear includes a large gear and a small gear, both mounted coaxially to the same shaft, having the large gear meshing to the driving gear; the small gear meshing to the rack; and the diameter of the driving gear being smaller than that of the large gear.

5. The optimized breast implant injector as claimed in claim 1, wherein the hollow tube body and the short tube reducer can be made as one piece.

6. The optimized breast implant injector as claimed in claim 1, wherein the outer surface of the push block appears to be a circular arc shape.

7. The optimized breast implant injector as claimed in claim 1, wherein the channel of the circular disk has a protruding shape.

8. The optimized breast implant injector as claimed in claim 1, wherein the bottom of the rack has a groove and a locking element is locked from the outer side of the housing to the inside of the groove.

9. The optimized breast implant injector as claimed in claim 1, wherein the outer of the driving device can be installed with a protective case.

* * * * *